United States Patent [19]

Grangirard et al.

[11] 4,177,801
[45] Dec. 11, 1979

[54] PROCESS AND APPARATUS FOR THE NON-INTRUSIVE MEASUREMENT OF CIRCULATORY PARAMETERS

[75] Inventors: Henri Grangirard, Villeurbanne; Pierre F. Serres, Sainte-Foy-les-Lyon, both of France

[73] Assignee: Dubernard Hospital, S.A., Bordeaux, France

[21] Appl. No.: 816,659

[22] Filed: Jul. 18, 1977

[30] Foreign Application Priority Data

Jul. 30, 1976 [FR] France .............................. 76 24233

[51] Int. Cl.² ............................................. A61B 5/02
[52] U.S. Cl. ...................................................... 128/681
[58] Field of Search ................... 128/2.05 A, 2.05 C, 128/2.05 E, 2.05 G, 2.05 M, 2.05 P, 2.05 Q, 2.05 T

[56] References Cited

U.S. PATENT DOCUMENTS

| | | | |
|---|---|---|---|
| 1,934,124 | 11/1933 | Hubbard | 128/2.05 Q |
| 2,720,113 | 10/1955 | Statham | 128/2.05 Q X |
| 2,848,992 | 8/1958 | Pigeon | 128/2.05 P |
| 2,865,365 | 12/1958 | Newland et al. | 128/2.05 A |
| 3,056,401 | 10/1962 | Greenspan et al. | 128/2.05 M X |
| 3,542,011 | 11/1970 | Langenbeck | 128/2.05 E |
| 3,633,568 | 1/1972 | Hobel | 128/2.05 M |
| 3,796,213 | 3/1974 | Stephens | 128/2.05 P X |
| 3,905,354 | 9/1975 | Lichowsky | 128/2.05 M |
| 3,996,926 | 12/1976 | Birnbaum | 128/2.05 A |
| 4,058,117 | 11/1977 | Kaspari et al. | 128/2.05 A |

FOREIGN PATENT DOCUMENTS 1221331  2/1971  United Kingdom ............... 128/2.05 M

OTHER PUBLICATIONS

Raines et al, "A Noninvasive Pressure Pulse Recorder . . . ", Med. Inst., vol. 7, No. 4, Sep.–Oct. 1973, pp. 245-250.

Primary Examiner—Lee S. Cohen
Attorney, Agent, or Firm—Mason, Kolehmainen, Rathburn & Wyss

[57] ABSTRACT

The invention relates to an apparatus and a process for measuring circulatory parameters by external route.

The apparatus of the invention consists of a pressure-applying device such as a cuff 1 to which is connected a Y-shaped tube 2 of which one of the branches 2a is connected to one pole 3a of an electronic differential pressure gauge 3, in itself already known, and the other branch 2b is connected to an airtight air-reservoir 4, there being situated on the said other branch between the air-reservoir and the pressure-applying device a device 5 for closing the said other branch together with the outlet 6 of an air-pump 7, the outlet of the said air-reservoir being connected to the other pole 3b of the differential pressure gauge.

The invention may be used for determining the shape, amplitude and frequency of the pulse, for monitoring variations in arterial pressure and for measuring and indicating digitally systolic, mean and diastolic pressures.

14 Claims, 10 Drawing Figures

PL. I-4

PL II - 4

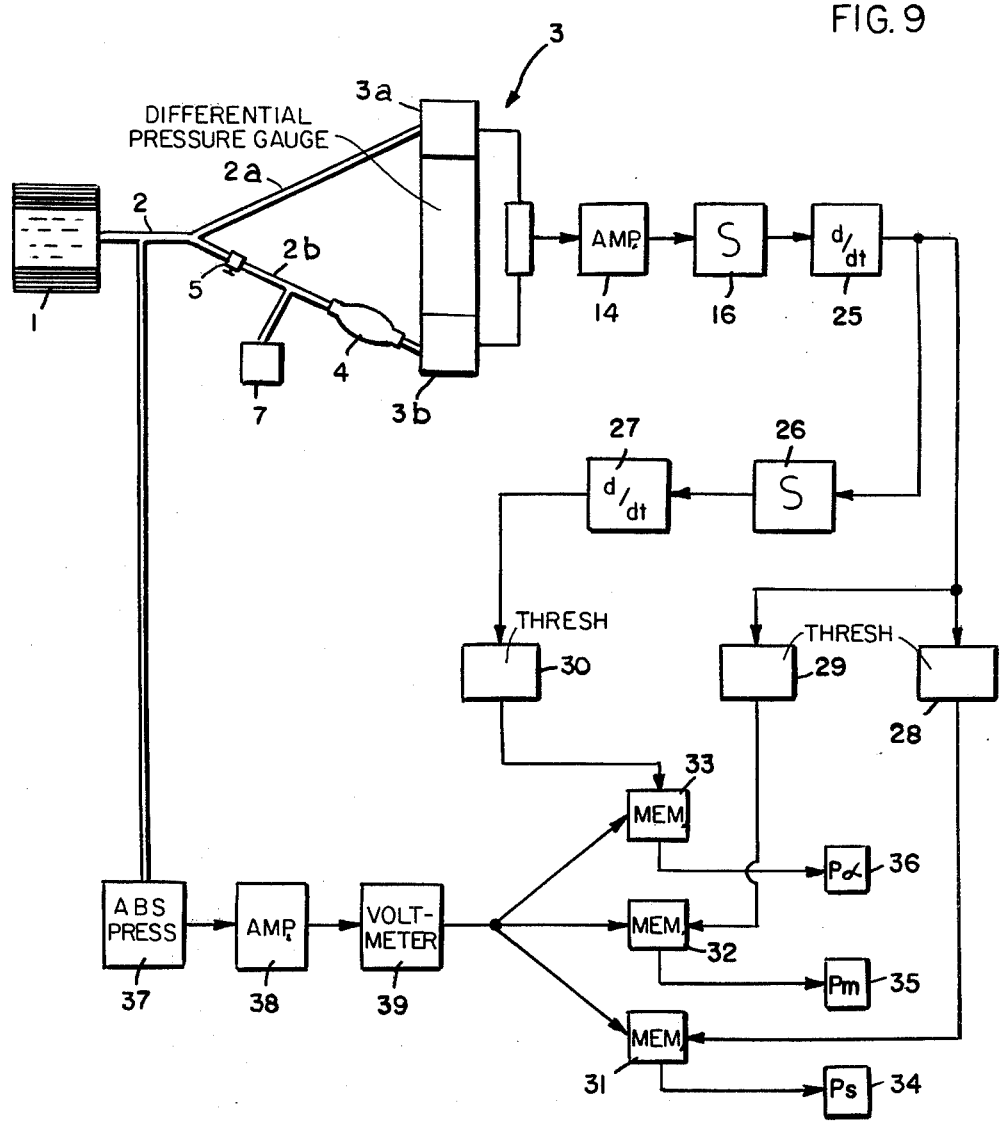

PROCESS AND APPARATUS FOR THE NON-INTRUSIVE MEASUREMENT OF CIRCULATORY PARAMETERS

The present invention relates to a process for the continuous measurement of circulatory parameters in a human or animal body by non-intrusive or external route, the said parameters being:

arterial pressure
pulse
certain cardiovascular values.

According to the result which it is desired to achieve the process of the invention may be employed for the purpose of:

performing continuous peripheral sphygmography i.e. determining in an uninterrupted manner the shape, amplitude and frequency of the pulse;

continuously monitoring variations in arterial pressure;

determining at fixed intervals and indicating digitally systolic, mean and diastolic pressures.

The invention also concerns an apparatus for carrying out the above process for the measurement of circulatory parameters in a continuous manner. The invention furthermore relates to improvements incorporated into the said apparatus with a view to effecting the following operations:

determining in a continuous manner the shape, amplitude and frequency of the pulse;

continuously monitoring variations in arterial pressure;

determining at fixed intervals and indicating digitally systolic, mean and diastolic pressures.

Apparatus for measuring each of the above circulatory parameters individually are already known but there does not exist any apparatus capable of providing such a plurality of results as that given by the apparatus of the invention.

It may be pointed out in this connection that the current methods of measuring arterial pressure, for example, by non-intrusive route are manual and that they only enable spot measurements to be made. They consist of closing an artery by applying considerable counter-pressure through an inflatable cuff and then allowing the counter-pressure to diminish so that parameters may be perceived which appear as a result of the intra-arterial turbulence thus created, for example Korotkoff sounds.

There also exists an automatic method of determining systolic and diastolic pressures by measuring Doppler shifts of sound waves relected by the artery. However, the use of this method is far from simple since it involves the careful positioning of a measuring apparatus with respect to the artery. Furthermore, this method only provides periodical data and the results are not registered digitally. Finally, it does not enable mean pressure to be measured.

In addition to the above, there exists an apparatus for monitoring mean pressure which functions on an oscillometric principle. However, this apparatus does not enable the other circulatory parameters cited above to be measured. Furthermore, it only operates at intervals and is not continuous.

Various apparatus enabling some of the above-mentioned circulatory parameters to be determined have been described, for example, in French Pat. Nos. 1,105,481; 1,258,471; 1,310,264 and in the first Certificate of Addition No. 63,604 to French Pat. No. 1,036,643.

These apparatus do not permit the plurality of circulatory parameters to be determined which can be measured by the apparatus of the invention. Furthermore, the data supplied by these apparatus are not very precise and are never registered digitally. In all these existing apparatus, the conversion to electrical values of pneumatic impulses supplied by the cuff is effected by mechanical or pneumatic devices.

The apparatus of the invention, which is also based on the conversion of pneumatic impulses to electrical values, employs for this purpose an electronic differential pressure gauge which is devoid of any mechanical element and, which although already known, has never been employed hitherto for the achievement of such a conversion in the field of application envisaged herein.

The apparatus of the invention enables the above-indicated disadvantages to be overcome by placing at the disposal of the clinician a single unit by which a plurality of circulatory parameters can be determined, measured or monitored by non-intrusive route and with a high degree of precision and simplicity of operation.

It is known that the distortion of the arterial wall produced by the variation in intra-arterial pressure occurring during the cardiac cycle causes a shock-wave to appear. This shock-wave is produced by two intra-arterial values which differ from each other according to the degree of pressure exercised on the artery.

The two values in question are, on the one hand, the normal intra-arterial pressure variation occurring during the cardiac cycle and, on the other, an induced intra-arterial turbulence or blood-disturbance.

If the artery is not compressed or is only slightly compressed, the blood inside the artery is considered to flow smoothly: turbulence is practically non-existent but the arterial wall is distorted at intervals by the systolic shock-wave.

On the other hand, if the artery is compressed, the smooth nature of the blood-flow is upset. Intra-arterial turbulence then appears which "punches" the arterial wall.

These two values, intra-arterial pressure and induced turbulence, together with their variations, will be used in different manners within the framework of the process of the invention.

The shock-wave produced by the periodic distortion of the arterial wall, itself provoked by the variations in intra-arterial pressure in the non-compressed artery or by the induced turbulence in the compressed artery, can be picked up by a ring of flexible material filled with air, such as, for example, a cuff fixed round a limb of the subject.

Here it should be pointed out that for greater simplicity the term "cuff" will be used hereinafter to designate the pressure-applying means employed for detecting the variations of pressure occurring in the artery. Although the usual means used for this purpose is an inflatable cuff made of flexible material, it is understood that the apparatus and process of the invention are not limited to this classical means and may be equally well operated with any pressure-applying means capable of performing the same function as the classical cuff. Similarly, the term "inner surface" applies to that part of the pressure-applying means which is in direct contact with the body of the subject. The term "subject" applies to the living creature, human or animal, of which the circulatory parameters are being measured or monitored.

The process of the invention for measuring circulatory parameters by non-intrusive route, as well as the apparatus designed for applying this process, is based on the principle that the shock-wave in question, when it is picked up by the inner surface of the cuff, previously inflated to a given pressure, produces on the said inner surface distortions which are proportional to the amplitude of the shock received. The distortions thus produced on the inner surface of the cuff provoke in their turn variations of pressure inside the cuff which are proportional to the amplitude of the shock received. These variations of pressure inside the cuff are then picked up by an electronic differential pressure gauge, which is in itself known, and subsequently converted to a continuous electronic signal of an intensity which is proportional to that of the pneumatic impulse received.

One object of the invention is to provide a process for measuring circulatory parameters by non-intrusive route, using a suitable device such as a cuff which can compress a part of the body of a subject to a selected degree, the said process consisting in the conversion of a shock-wave, caused by normal or induced intra-arterial phenomena, to an electrical value, such as, for example, a difference in potential, by means of an electronic differential pressure gauge, which is in itself already known, the said electrical value being supplied in a continuous manner and with a degree of amplitude which is proportional to that of the pneumatic impulse received and consequently proportional to the intensity of the intra-arterial phenomena.

The process in question can be performed by either isolating or not isolating one of the two poles of the electronic differential pressure gauge from the cuff.

When one of the said poles is isolated from the cuff, the electronic differential pressure gauge measures the variations in the counter-pressure due to the intra-arterial phenomena in comparison with a constant reference pressure.

On the other hand, when neither of the said poles is isolated from the cuff, the variations in the counter-pressure in the cuff due to the intra-arterial phenomena are picked up by the two poles of the electronic differential pressure gauge.

However, one of the poles receives the variations in question of the counter-pressure after they have undergone linear modification by a factor $\alpha$ after passing through an airtight air-reservoir connected to the pole in question.

The differential pressure gauge measures the variations in the counter-pressure due to the intra-arterial phenomena, the said variations being modified by a factor $|\alpha - 1|$.

Another object of the invention is to provide an apparatus for measuring circulatory parameters by non-intrusive route, the said apparatus consisting essentially of an inflatable cuff to which is attached, in an airtight manner, a tube in the form of the letter "Y" of which one of the branches is attached to one pole of an electronic differential pressure gauge, which is in itself already known, the other branch being connected to an airtight air-reservoir, there being provided between the air-reservoir and the cuff the outlet-tube of an air-pump and a means for closing the said other branch, the said air-reservoir being fitted with an outlet tube which is connected to the other pole of the electronic differential pressure gauge.

As a means for closing said other branch there may be used, for example, a tap or an electronically controlled valve.

In accordance with one particular embodiment of the apparatus of the invention, the outlet-tube of the air-pump may be placed directly at the outlet of the cuff or on that branch of the Y-shaped tubing which is not connected to the airtight air-reservoir.

In accordance with another embodiment of the apparatus of the invention, the air-reservoir is omitted, the cuff being connected by the Y-shaped tubing to the electronic differential pressure gauge as described above. This variation of the apparatus will only be employed when the process for measuring the circulatory parameters is carried out by isolating one of the poles of the electronic differential pressure gauge from the cuff.

In accordance with a further embodiment of the apparatus of the invention, the means for closing one of the branches of the Y-shaped tubing is omitted.

This latter variation can be used, for example, in those cases where the process for measuring the circulatory parameters can be carried out without first isolating one of the poles of the electronic differential pressure gauge from the cuff. According to the circulatory parameters which are to be determined, the process of the invention will include a series of additional operations selected in accordance with the final result to be achieved.

Similarly, the apparatus of the invention will include additional devices according to the circulatory parameters to be determined.

As indicated above, the process of the invention makes different uses of the shock-wave produced against the arterial wall by the blood-flow, according to whether this shock-wave is caused by the behaviour of the intra-arterial pressure during the cardiac cycle or by the turbulence induced by compression of the artery.

Thus, use will be made of the variations in intra-arterial pressure in a non-compressed artery transmitted to a cuff inflated to a constant pressure which is well below the diastolic pressure of the subject in order to visualize and/or register in a continuous manner the shape, amplitude and frequency of the pulse.

The process of the invention when used for the purpose of visualizing and/or registering, in a continuous manner, the shape, amplitude and frequency of the pulse will consist of first applying to the two poles of the electronic differential pressure gauge a pressure equal to the counter-pressure existing in the cuff, the said counter-pressure being maintained constant and below the diastolic pressure of the subject, of isolating from the cuff the pole of the gauge which is connected to the air-reservoir so that the normal intra-arterial phenomena producing variations in the counter-pressure in the cuff may be picked up by the other pole of the said gauge and converted to a continuous electrical value proportional to the intensity of the intra-arterial phenomena, then visualizing and/or registering in a continuous manner the desired circulatory parameters.

Preferably, the electrical value issuing from the electronic differential pressure gauge will be amplified before further treatment.

The apparatus of the invention, when adapted to determine the shape, amplitude and frequency of the pulse, in accordance with the process described above, will comprise, in addition, at the outlet of the electronic differential pressure gauge, means for visualizing and/or registering the electrical signal issuing from the said gauge.

As visualization system, use could be made of, for example, an oscilloscope while registration could be effected by any type of classical registration means such as for example a pen-registration-unit.

As regards the frequency of the pulse, this could be visualized by means of a classical frequencymeter or one equipped with digital registration means.

Preferably, the apparatus will also include electronic amplifying means connected to the outlet of the electronic differential pressure gauge and to the means for visualization and/or registration.

The sphygmograph so conceived enables the desired circulatory parameters to be determined in a continuous manner by non-intrusive and consequently non-traumatic route.

The constant counter-pressure maintained in the cuff is very slight being in the region of 15 mm Hg when the latter is applied to the carotid and of 30 to 40 mm Hg when it is attached to a limb. In this way, neither the arterial nor the venous circulation is disturbed.

The sphygmographs employed at present are very delicate to operate. They require very exact positioning of the cuff. This disadvantage is avoided with the sphygmograph of the invention, since the sensitivity of the latter is so great that it enables even very slight modifications in the parameters registered to be detected. Furthermore, the precision of the tracings under such simple conditions of operation, is remarkable. These tracings enable other sphygmographic data to be obtained than those cited above, such as, for example, respiratory frequency.

The spygmograph of the invention may be used for cardiovascular haemodynamic examinations in human and veterinary medicine and for monitoring peripheral circulation.

In addition to the determination of the shape, amplitude and frequency of the pulse, the process of the invention can be used to determine other circulatory parameters.

Thus, the process of the invention when used in other applications makes it possible both to monitor in a continuous manner variations in arterial pressure and to determine automatically and periodically systolic, mean and diastolic pressures.

For the purpose of monitoring in a continuous manner variations in arterial pressure, use will be made of the variations in maximum amplitude of the intra-arterial pressure in an artery submitted to continuous constant pressure which is well below the diastolic pressure of the subject. On the other hand, for the purpose of periodically measuring systolic, mean and diastolic pressures, use will be made of the variations in the amplitude of the intra-arterial turbulence in an artery which is decompressed from a suprasystolic pressure to an infradiastolic pressure.

Curve (1) of FIG. 1 represents the variations in the amplitude of the induced turbulence in an artery or the variations in the amplitude of the shock-wave striking the inner surface of the cuff as a function of the counter-pressure P applied to the artery by the cuff in question from a suprasystolic pressure to an infradiastolic pressure.

The general form of the curve (1) of FIG. 1 perfectly reflects the experimental findings described below.

If an external pressure is applied to an artery by means, for example, of a cuff inflated to a pressure which is sufficient to close completely the artery, the blood can no longer circulate freely and no pulsatile movement is transmitted to the cuff. If the artery-closing pressure is gradually diminished, the artery tends to reopen. At the instant of reopening, the value of the counter-pressure in the cuff corresponds to the systolic pressure of the subject. If the counter-pressure is further reduced, the turbulence induced in the artery increases as does the amplitude of the shock-wave against the wall of the artery which is expressed as a variation in pressure picked up by the inner surface of the cuff. If the counter-pressure continues to diminish, the blood turbulence passes through a maximum of intensity. At this moment, the counter-pressure in the cuff corresponds to the mean arterial pressure of the subject. Continued reduction of the counter-pressure then leads to a reduction of the induced intra-arterial turbulence and, consequently, to a reduction of the amplitude of the shock-wave thus produced.

At a given moment, the intra-arterial turbulence suddenly fades and the blood-flow becomes practically smooth again. At this moment, the counter-pressure corresponds to the diastolic pressure of the subject.

If it is supposed that the arterial pressure of the subject does not vary, the general form of the curve of variation of intra-arterial turbulence as a function of a new suprasystolic counter-pressure followed by a reduction of this counter-pressure to an infradiastolic value will coincide exactly with curve (1) of FIG. 1.

If, for any reason, the arterial pressure of the subject should change, this change will produce a lateral displacement of curve (1) along the axis of the counter-pressures. A drop in the arterial pressure of the subject will be expressed as a displacement of curve (1) towards the left i.e. curve (2) while a rise in arterial pressure will lead to a displacement of curve (1) towards the right i.e. curve (3).

Consequently, any drop in arterial pressure when there is a constant counter-pressure in the cuff will produce an increase in the intra-arterial phenomenon measured and conversely any rise in the arterial pressure of the subject will lead to a reduction in the intra-arterial phenomenon measured.

The process of the invention, when applied to the continuous monitoring of variations in arterial pressure will consist in maintaining the counter-pressure in the cuff at a constant value which is below the diastolic pressure of the subject, in isolating or not isolating from the cuff one of the two poles of the electronic differential pressure gauge so that the intra-arterial phenomena producing variations in the counter-pressure in the cuff may be picked up by the said gauge and converted to a continuous electrical value which is proportional to the intra-arterial phenomena, in integrating, with respect to time, the electrical value thus produced and then setting off a visual and/or audible alarm for any change of amplitude of the integrated electrical value.

Preferably, the electrical value issuing from the differential pressure gauge will be amplified before integration.

The apparatus of the invention, when adapted for monitoring in a continuous manner variations in arterial pressure in accordance with the process described above, will comprise, in addition, at the outlet of the electronic differential pressure gauge, an integrating circuit, with respect to time, for the electrical impulses issuing in a continuous manner from the said gauge, followed by means for detecting, at adjustable thresholds, the variations of amplitude of the integrated electrical value, the said means being capable of setting off a visual and/or audible alarm and comprising means capable of eliminating the artifacts i.e. the short-lived variations in electric amplitude resulting from brief variations in the integrated electrical value caused by movements on the part of the subject.

Advantageously, the apparatus so conceived will also comprise electronic amplification means connected, on the one hand, to the outlet of the electronic differential pressure gauge and, on the other, to the integrating circuit.

When the above-described apparatus is operated after closure of that branch of the Y-shaped tubing which is connected to the air-reservoir, the electronic differential pressure gauge plays the part of an electronic absolute pressure gauge.

It is clear that, in these circumstances, the electronic differential pressure gauge could be replaced by an electronic- or pneumatic-type absolute pressure gauge.

To provide an improved version of the above-described apparatus for the continuous monitoring of arterial pressure, the means for detecting variations in amplitude is connected to any suitable system for visualizing and/or registering arterial pressure.

To provide yet another improved version of the above-described apparatus, there are attached to the outlet of the electronic differential pressure gauge means capable of visualizing and/or registering the shape, amplitude and frequency of the pulse.

The apparatus of the invention, when adapted for monitoring variations in arterial pressure functions by external or non-traumatic route.

The constant counter-pressure maintained in the cuff is sufficiently weak not to hinder either arterial or venous circulation.

The apparatus in question is very easy to operate and is very sensitive. It enables, for example, rises and drops in diastolic pressure to be detected with considerable sensitivity. For example, it can detect a variation in diastolic pressure as slight as ±1 mm Hg.

The apparatus of the invention when adapted for monitoring variations in arterial pressure can be used in the same specialized medical fields as the above-described sphygmograph.

Furthermore, the apparatus in question will be equally useful in both human and veterinary medicine, as well as in pharmacological research for the study, for example, of hypotensive products.

The automatic and periodical measurement of systolic, mean and diastolic pressures by means of the process of the invention together with their digital indication is based on the use of the curve of FIG. 2 which represents the variations of the amplitude of the electrical impulses issuing from the differential pressure gauge as a function of the variations in counter-pressure in the cuff from a value higher than the systolic pressure of the subject to a value lower than the diastolic pressure of the subject in question.

Systolic pressure (Ps), mean pressure (Pm) and diastolic pressure (Pd) each correspond to one of the three points characterizing the curve of FIG. 2, these points themselves corresponding to alterations in the ramp of the curve.

The principle underlying the measurement of the systolic, mean and diastolic pressures of a subject, by means of the process of the invention, will consist essentially in causing the counter-pressure in the cuff to vary from a suprasystolic value to an infradiastolic value while indicating digitally the values of the counter-pressure in the cuff which correspond to points Ps, Pm and Pd on the curve of FIG. 2.

The process of the invention, when applied to the periodical and automatic determination as well as to the digital indication of systolic, mean and diastolic pressures will consist in causing the counter-pressure in the cuff to vary from a value above the systolic pressure of the subject to a value below the diastolic pressure of the same subject, in isolating or not isolating one of the poles of the electronic differential pressure gauge from the cuff so that the intra-arterial phenomena which cause variations in the counter-pressure in the cuff may be picked up by the said gauge and converted to a continuous electrical value which is proportional to the intra-arterial phenomena, in picking up in a continuous manner the instantaneous counter-pressures existing in the cuff and converting them to an electrical value by means of an electronic absolute pressure gauge connected to the latter, the said electrical value being transmitted in a continuous manner with an amplitude which is proportional to the pneumatic impulse received, in picking up simultaneously and electronically data at the three points characterizing the curve of variations in the amplitude of the electrical value issuing from the electronic differential pressure gauge as a function of the counter-pressure in the cuff and in indicating digitally the three values of the counter-pressure existing in the cuff which correspond to the three points alluded to above and which indicate the systolic, mean and diastolic pressures.

Preferably, the electrical values issuing from the electronic differential pressure gauge and from the electronic absolute pressure gauge respectively will be amplified before further treatment.

The electronic means of obtaining the data referred to above and the precise use made of these data will be described in detail below.

FIG. 2 represents the mathematically conceived outline of the amplitudes "a" of the electrical value issuing from the electronic differential pressure gauge as a function of the counter-pressure "P" existing in the cuff.

The derivative da/dP leaves the value zero at Ps, returns to zero and changes its sign at Pm and becomes very great at Pd.

The derivative da/dP may be converted to a mathematical derivative of the amplitude "a" with respect to time T, in accordance the following equation:

$$\frac{da}{dP} = \frac{da}{dT} \times \frac{dT}{dP} \text{ which is the same as:}$$

$$\frac{da}{dP} = \frac{\frac{da}{dT}}{\frac{dP}{dT}} = \frac{\frac{da}{dT}}{\text{speed of deflation of the cuff}}$$

The speed of deflation of the cuff, though not playing any part in the determination of Ps and Pm must, on the other hand, be as slow as possible to enable Pd to be determined with precision.

This speed of deflation of the cuff can be kept constant throughout the operation so that the derivative da/dP can be assimilated to K(da/dT), K being a constant value.

From the electronic viewpoint, account will not be taken of da/dP but of the differential:

$$\frac{\Delta a}{\Delta P} = \frac{\frac{\Delta a}{\Delta T}}{\frac{\Delta P}{\Delta T}}$$

In this equation Δ a represents the difference between the electrical value amplitudes at instants T+Δ T and T while Δ P represents the difference between the counter-pressure in the cuff at instants T+Δ T and T.

For greater facility, a time interval Δ T will be selected which is constant and equal, for example, to the interval between two heart-beats. Furthermore, as the deflation speed of the cuff is chosen so as to be slow and constant during the operation, Δ P is itself assimilated to a constant value.

In consequence, subsequent reasoning may be based on the Δ a values only.

It may be observed that at Ps, Δ a leaves a value which is practically nil for a positive value, that at Pm, Δ a returns to zero and changes its sign and that at Pd, Δ a becomes very great.

The electronic process described hereunder aims at obtaining solely at Ps, Pm and Pd, Δ a values leaving zero and crossing an amplitude value threshold previously programmed.

To this end, the differences in amplitude Δ a of the electric impulses represented in FIG. 2 are converted to "staircase-form" signals. This "staircase" effect which develops as shown in FIG. 3 is obtained by means of an integrating circuit containing a dephasing element. The height of each signal forming part of the "staircase" illustration is proportional to Δ a and has the same sign.

The "staircase-form" signals of FIG. 3 are then differentiated with respect to time, which gives a series of very brief impulses which are proportional to the distance between each step of the "staircase". These impulses behave as illustrated in FIG. 4.

Point A of FIG. 4 represents the moment when the impulses appear i.e. when they leave a zero value. As shown by FIG. 4, the axis of the zero amplitudes is situated on the axis of the abscissae.

Point A corresponds to the systolic pressure.

Point B represents the moment when the impulses change sign i.e. pass through a zero value and leave it while retaining the sign resulting from the change.

Point B corresponds to the mean pressure.

To detect Point C where the amplitude of the impulse is negative and maximum, processes similar to those which have made it possible to pass from FIG. 2 to FIG. 4 are applied to the negative impulses of FIG. 4, these negative impulses being first rendered positive but without any dephasing.

At Point D, there is, as at Points A and B, an amplitude of impulse which passes through a zero value and leaves it. The result thus obtained is illustrated in FIG. 5.

Point D represents the diastolic pressure of the subject.

At the moment when the impulse at Point A crosses the corresponding threshold of amplitude previously programmed and represented in FIG. 4 by a broken line, a very brief electrical impulse is emitted which blocks an electronic memory-unit. The same process is applied to Points B and D respectively so that two other memory-units can be blocked.

During the deflation of the cuff from a suprasystolic pressure to an infradiastolic pressure, the instantaneous pressure is picked up in a permanent manner in the interior of the cuff and converted, by means of an electronic absolute pressure gauge, to a continuous electrical value of an amplitude which is proportional to the pneumatic impulse received. This electrical value then passes through a numerical volt-meter and the information thus obtained is then transferred to the three memory-units alluded to above, each of which is followed by a digital indicator.

At the moment when each of these three memory-units is blocked, the digital information corresponding to the pressure in the cuff at this instant is indicated. As the memory-units are blocked only at the Points A, B and D of FIGS. 4 and 5, the instantaneous pressures in the interior of the cuff at the moments when the memory-units are blocked correspond to the systolic, mean and diastolic pressures of the subject.

The apparatus of the invention, when adapted for the periodical and automatic measurement of the systolic, mean and diastolic pressures and for their digital indication, will further comprise, on the one hand, an electronic absolute pressure gauge connected to the cuff and to a numerical voltmeter which is itself connected to three memory-units each of which is followed by a system of digital indication and, on the other hand, at the outlet of the electronic differential pressure gauge, means for integration to "staircase-form" signals, the amplitude of these signals being proportional to the electrical impulses issuing from the said differential pressure gauge together with means for differentiating, with respect to time, the fresh impulses thus received, these means for differentiating being themselves connected to three amplitude threshold systems previously programmed, each of these latter being connected to one of the three memory-units.

A first means of integration is connected to a first means of differentiation which itself is connected to two of the three threshold systems in question with a view to the later digital indication of the systolic and mean pressures.

In addition, the first means of differentiation is connected to a second means of integration to "staircase-form" signals followed by a second means of differentiation itself connected to an amplitude threshold system previously programmed with a view to the later digital indication of the diastolic pressure.

Advantageously, the apparatus so conceived will comprise, in addition, means for electronic amplification situated immediately after the outlets of the electronic differential pressure gauge and of the electronic absolute pressure gauge.

When the apparatus described above is utilized for the purpose of determining arterial pressure after closure of that branch of the Y-shaped tubing which is connected to the air-reservoir, the electronic differential pressure gauge plays the part of an electronic absolute pressure gauge.

It is clear that, under these circumstances, the electronic differential pressure gauge could be replaced by an electronic or pneumatic absolute pressure gauge.

In reality, any pressure gauge which is capable of providing, at its outlet, an electrical value of which the amplitude corresponds to the curve of FIG. 2 as a function of the counter-pressure in the cuff can replace, in this application, the electronic differential pressure gauge in question.

Similarly, any pressure gauge capable of transforming the counter-pressures in the cuff into a value which is continuous and proportional to the latter can be used in place of the electronic absolute pressure gauge envisaged for this purpose.

The apparatus of the invention thus adapted for determining systolic, mean and diastolic pressures operates by external non-traumatic route.

Its use is both simple and precise. It enables systolic, mean and diastolic pressures to be determined and indicated to within ±2 mm Hg both in human and veterinary medicine. In this respect, the apparatus of the invention is superior to the known apparatus used in this indication. Furthermore, its system for indicating results is completely new and enables the figures for mean pressure to be visualized.

It may be added that it is possible to combine in one single apparatus, the apparatus of the invention adapted for measuring arterial pressure with that for monitoring variations in this same arterial pressure.

To the apparatus of the invention adapted for measuring arterial pressure, may be added, at the outlet of the differential pressure gauge, an integrator, with respect to time, of the electric impulses issuing from the said gauge followed by means for detecting with adjustable thresholds variations in the amplitude of the integrated electrical value, these means being capable of setting off a visual and/or audible alarm.

Furthermore, there could be placed at the outlet of the first integrator of "staircase-form" signals incorporated in the apparatus for measuring arterial pressure, means for detecting with adjustable threshold variations in the amplitude of the integrated electrical value, the said means being capable of setting off a visual and/or audible alarm.

Thus, there has been conceived one single apparatus enabling variations in arterial pressure to be monitored, for example, between two determinations and indications of the said pressure.

It is also possible to add, at the outlet of the electronic differential pressure gauge, in the case of the two variations described above, means capable of visualizing and/or registering the shape, amplitude and frequency of the pulse.

Such an apparatus will consequently be useful for determining the shape, the amplitude and the frequency of the pulse as well as the systolic, mean and diastolic pressures. Furthermore, this apparatus will enable variations in arterial pressure to be monitored.

All the variations described above of the apparatus of the invention are also included within the scope of the present invention.

It can be added that in the apparatus of the invention, in its improved embodiments described above and in all their variations, it is possible to render certain operational phases automatic.

For example, an electronic system can be provided which enable the cuff to be inflated to a predetermined pressure and the closing-device fixed on one of the branches of the Y-shaped tubing to be automatically operated.

Similarly, the inflation and deflation of the cuff in accordance with a pre-programmed frequency can be made automatic.

The characteristics and advantages of the invention will, moreover, be made clear by the description given hereunder, for exemplifying purposes, with reference to the attached drawings in which:

FIG. 1, as already indicated, represent curves of variations of the intra-arterial turbulence induced as a result of the counter-pressure exercised by a cuff compressing an artery. These curves also represent the variations in the amplitude of the electrical value issuing from the electronic differential pressure gauge after integration with respect to time.

FIG. 9 is a diagrammatic representation of the apparatus of the invention adapted for the periodical determination and indication of the systolic, mean and diastolic pressures.

Figure 6:
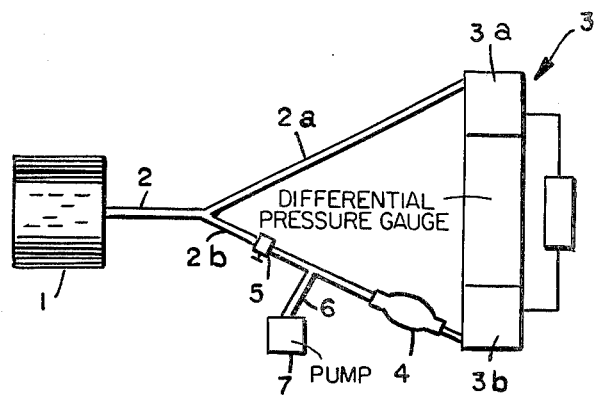
FIG. 6 is a diagrammatic representation of the apparatus of the invention.

In accordance with the embodiment illustrated in FIG. 6, an apparatus of the invention for measuring circulatory parameters by external route comprises a cuff 1 in the form of a circular hollow envelope in flexible material such as plastic or rubber of which the interior airtight cavity is connected to a tube 2 divided into two branches 2a and 2b. Branch 2a leads directly to pole 3a of apparatus 3 while branch 2b is connected to the inlet of an airtight air-reservoir the outlet of this reservoir being connected to pole 3b of apparatus 3. A tap 5 is incorporated in branch 2b. To the latter branch is attached on the opposite side of the tap to that on which the cuff is situated the outlet tube of an air-pump 7.

Apparatus 3 is preferably an electronic differential pressure gauge, which is in itself already known. From two different pressures received this gauge emits an electronic signal which is proportional to the difference between the pressures in question which are received by poles 3a and 3b respectively. Apparatus 3 may be, for example, the apparatus commercialized under reference L X 3700 D by the American Company National Semi-Conductor which consists of a Wheatstone bridge comprising four piezo-resistances. Poles 3a and 3b of this electronic differential pressure gauge are, in reality, two neighbouring piezo-resistances of the Wheatstone bridge comprising four piezo-resistances referred to above.

For apparatus 3, use can also be made of the system commercialized by Crouzet or Schlumberger i.e. comprising either a bridge with four piezo-resistances in which an amplifier may be incorporated with a thermostatic circuit or a high frequency system producing a phase displacement proportional to the differences in pressure.

Tube 2 is preferably of flexible material such as rubber and the interior diameter of the tube-circuit is about 2 mm.

The air-reservoir may be, for example, a cavity such as a hollow sphere or a hollow cylinder made of glass such as a resonator of the Helmoltz type. It may also consist of a series of hollow cavities.

The tap 5, may be, for example, a simple manually-operated tap or preferably an electronically controlled valve.

The following is a description of the functioning of the apparatus of the invention.

When the cuff has been fixed on the selected part of the subject's body, pump 7 is started, tap 5 being open. The cuff is inflated to a given pressure which is identical in the cuff and at the two poles 3a and 3b of apparatus 3. The tap is then closed. The pressure remains the same at pole 3b by reason of the airtightness of the pump 7. The air-reservoir 4 only serves as a reference pressure so as to compensate for any lack of airtightness in the pump.

The pressure variations due to the intra-arterial phenomena produce a shock-wave which is received by the arterial wall and thence transmitted to the inner surface of the cuff causing slight variations of pressure in the interior cavity of the latter. The pressure in the cuff, increased by the slight pressure variations due to the intra-arterial phenomena, is transmitted to pole 3a.

The difference in pressure at poles 3a and 3b after amplification upsets the Wheatstone bridge comprising four piezo-resistances of apparatus 3, which generates an electric charge.

The electric charge at the outlet of apparatus 3 is continuous and proportional to the variations in pressure due to the intra-arterial phenomena.

The apparatus of the invention can also function with tap 5 being open throughout the whole operation.

In this latter case, the initial pressure in the cuff, increased by the variations in pressure due to the intra-arterial phenomena, is transmitted on the one hand to pole 3a and on the other to the air-reservoir 4 which modifies linearly, by a factor $\alpha$, the amplitude of the vibratory phenomenon of constant frequency. In this way, the air-reservoir plays the role of resonator.

The modification coefficient $\alpha$ in question is as follows:

$$\alpha \simeq Q/\sqrt{(1-\mu^2)+4\epsilon^2\mu^2}$$

in which:
Q = number of resonating cavities $$\mu = \frac{\text{Cardiac frequency } (\simeq 1,2 \text{ Hertz}) \text{ or its harmonics}}{\text{Resonance frequency peculiar to the resonator}}$$

$\epsilon$ = Dampening coefficient of the resonating system $\epsilon < 2\%$ if glass and rubber are used.

The electronic differential pressure gauge 3 then mesures the difference between the pressures present at poles 3a and 3b, multiplies it by a coefficient K and converts it to an electrical value as previously described.

Figure 7:
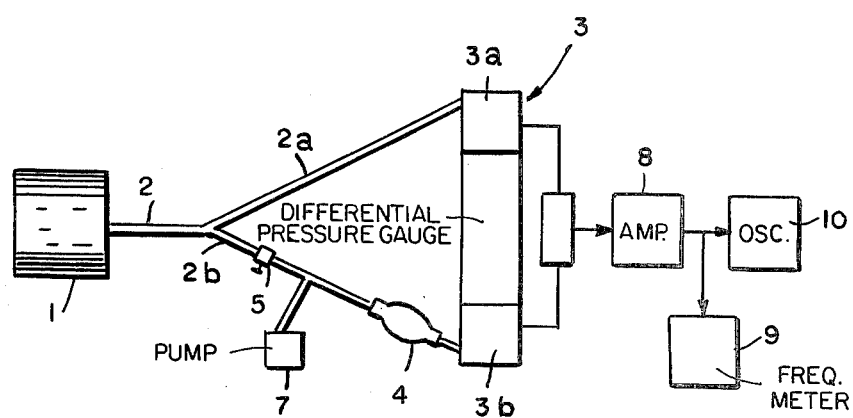
FIG. 7 is a diagrammatic representation of the sphygmograph of the invention.

The sphygmograph of the invention, in accordance with the embodiment represented by FIG. 7, comprises the cuff 1, the tubing 2 divided into its two branches 2a and 2b, the tap 5, the air-pump 7, the air-reservoir 4 and the electronic differential pressure gauge 3 with its two poles 3a and 3b. In addition, at the outlet of apparatus 3 there is an electronic amplifying system 8 such as an electronic amplifier formed of one or more linear stages of amplification with integrated circuits, followed by a frequencymeter 9 and by a graphic- or oscilloscopic-type registration-unit 10.

The functioning of the sphygmograph thus conceived may be described as follows.

The cuff 1 is placed on the selected part of the subject's body and the pump 7 is started, the tap 5 being open. The cuff is inflated to an interior pressure well below the diastolic pressure of the subject (about 15 mm Hg). The tap 5 is then closed. The differential pressure gauge 3 measures the difference between the pressures existing at poles 3a and 3b, it multiplies this difference by a coefficient K and converts it to an electrical value which is transmitted to the electronic amplifier 8. The amplified signal is then transmitted to the frequencymeter 9 which indicates cardiac frequency and to the registration-unit 10 of which the pen traces curves representing the shape of the pulse.

Figure 8:
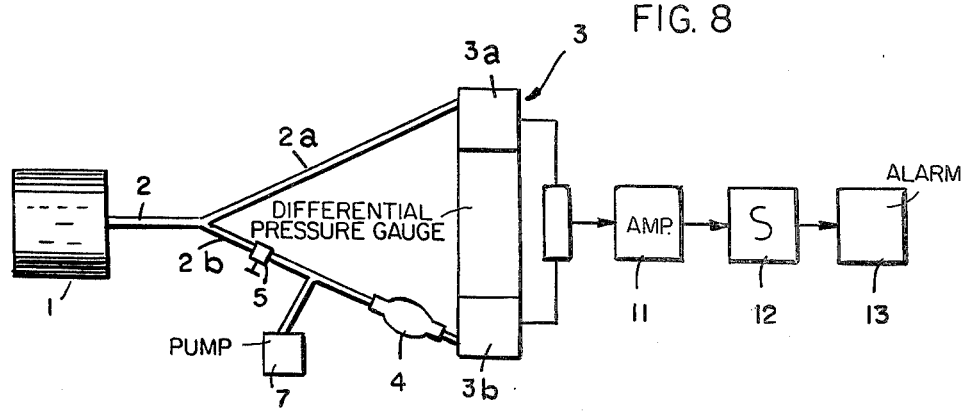
FIG. 8 is a diagrammatic representation of the apparatus of the invention adapted for the continuous monitoring of variations in arterial pressure.

In accordance with the embodiment illustrated by FIG. 8, an apparatus of the invention for monitoring variations in arteriel pressure comprises the cuff 1, the tube 2 divided into its two branches 2a and 2b, the tap 5, the air-pump 7, the air-reservoir 4, and the electronic differential pressure gauge 3 with its two poles 3a and 3b. In addition at the outlet of element 3 is placed an electronic amplifying system 11 such as an electronic amplifier formed of one or more linear amplifying stages with integrated circuits, for example, a SFC 2741 EC amplifier marketed by the Company Sescosem. The amplifier 11 is itself connected to an integrator 12 of classical design followed by an alarm system 13 with adjustable threshold which detects and compares amplitudes of electric impulses at a predetermined level of amplitude. The alarm system in question provides audible and/or luminous signals for amplitudes of electric impulses which are of sufficient duration and exceed the threshold amplitude.

The apparatus thus conceived for the continuous monitoring of variations in arterial pressure functions as follows.

For purposes of illustration, the functioning and use of this apparatus for monitoring a drop in arterial pressure has already been described.

The cuff 1 is placed round a limb of the subject. The tap 5 being, for example, open, the pump 7 is started and the cuff inflated until a constant pressure is obtained in the interior of the latter which is below the diastolic pressure of the subject.

The differential pressure gauge 3 measures the difference between the pressures existing at poles 3a and 3b and, as described above, converts this difference to an electrical value. The electrical impulses issuing from the amplifier 11 are then integrated as regards their surfaces with respect to time by means of the integrator 12 to give a level which is continuous and proportional to the surface area of the impulse. The electrical value at the outlet of the integrator 12 is then transmitted to the alarm system 13. The alarm functions when the amplitude of the current reaches a predetermined threshold during a sufficiently long period of time, for example, 5 or 6 seconds.

Figure 1:
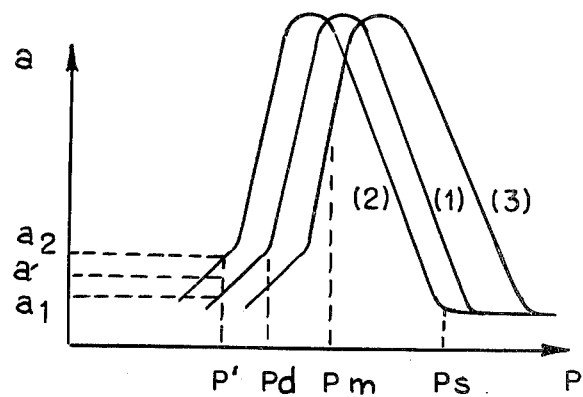

In FIG. 1, it has been supposed that $a_1$ represents, for a counter-pressure P' in the cuff, the amplitude of the electrical value at the outlet of the integrator at the beginning of the operation. The operator will program, as threshold amplitude, for example, the value of the amplitude $a' > a_1$.

If the arterial pressure of the subject drops during the experiment, the curve (1) obtained in the test shifts to the position occupied by curve (2) for example. In this case, the alarm will function for the amplitude $a_2 > a'$.

In accordance with the embodiment illustrated in FIG. 9, an apparatus of the invention for determining and indicating systolic, mean and diastolic pressures comprises the cuff 1, the tube 2 divided into its two branches 2a and 2b, the tap 5, the air-pump 7, the air-reservoir 4 and the electronic differential pressure gauge 3 into its two poles 3a and 3b.

In addition, at the outlet of the element 3 there is an electronic amplifying system 14 such as an electronic amplifier formed of one or more linear amplifying stages with integrated circuits, for example, a SFC 2741 EC amplifier.

Figure 10:
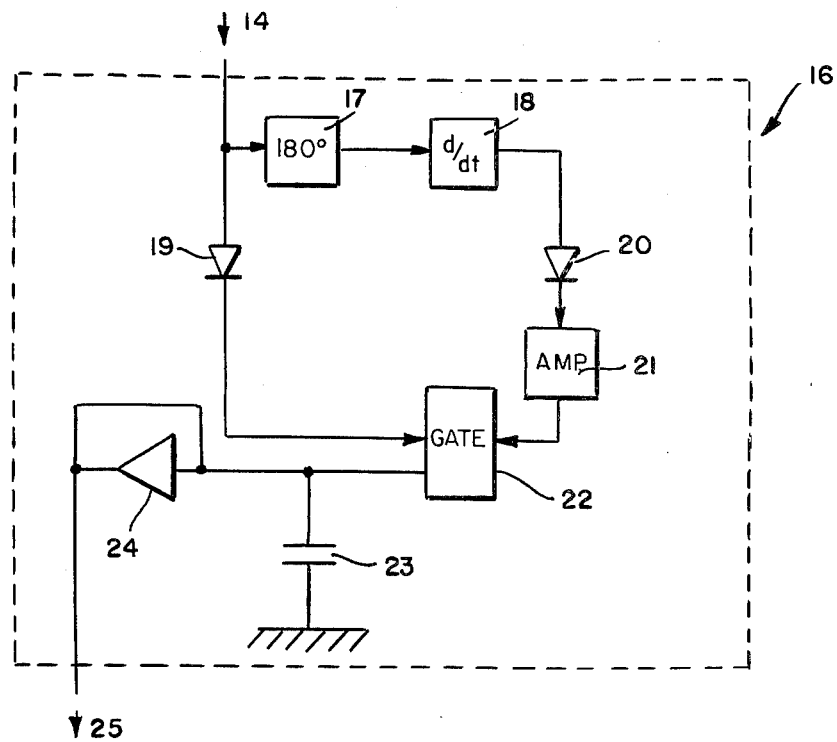
FIG. 10 is a diagrammatic representation of an integrator giving "staircase-form" signals.
Figure 2:
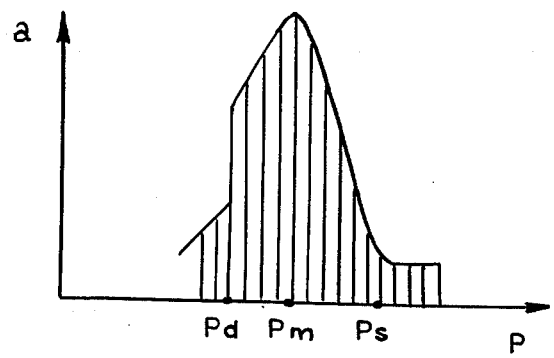
FIG. 2 represents the mathematically conceived outline of the amplitude "a" of the electric impulses issuing from the differential pressure gauge as a function of the counter-pressure "P" in the cuff.
Figure 3:
FIG. 3 represents a diagram of amplitudes "a" obtained after integration of the amplitudes of FIG. 2 to "staircase-form" signals as a function of the counter-pressure "P" in the cuff.
Figure 4:
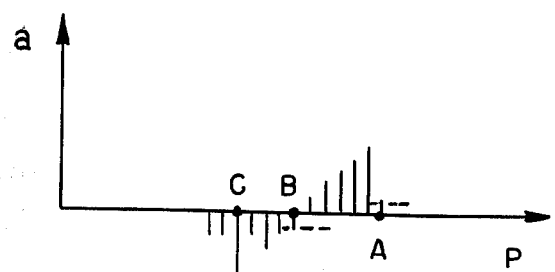
FIG. 4 represents a diagram of amplitudes "a" obtained after differentiation, with respect to time, of the "staircase-form" signals represented in FIG. 3 as a function of the counter-pressure "P" in the cuff.
Figure 5:
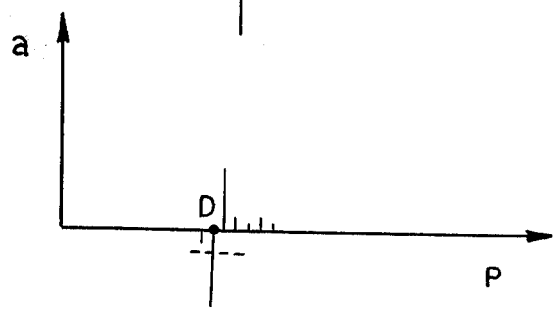
FIG. 5 represents a diagram of amplitudes "a" obtained after integration of the negative amplitudes of FIG. 4 to "staircase-form" signals followed by differentiation, with respect to time, of these "staircase-form" signals as a function of the counter-pressure "P" in the cuff.

The amplifier 14 is itself connected to a first integrator 16 of "staircase-form" signals. An integrator of this type is represented in FIG. 10. It comprises the dephasing unit 17 of $\pi/2$ composed of a condenser and an amplifier without counter-reaction, the classical-type differentiatior 18 formed of a condenser and a resistance, the diodes 19 and 20, the electronic amplifier 21, the gate 22, the condenser 23 and the amplifer 24 mounted as an impedance adapter.

The integrator 16 is connected to a first classical-type differentiator 25. Following the differentiator 25 there is a second integrator 26 of "staircase-form" signals identical to element 16. Following this integrator 26, there is the differentiator 27. The two differentiators 25 and 27 are themselves connected to threshold amplitude circuits. The differentiator 25 is connected to the threshold circuit 28 of the systolic pressure and to the threshold circuit 29 of the mean pressure while the differentiator 27 is connected to the threshold circuit 30 of the diastolic pressure.

These threshold circuits are so constituted that the impulses issuing from the differentiators are transmitted in opposition to a threshold electrical value. Only the impulses issuing from the differentiators which are superior to the electrical counter-value can pass to an amplifier.

The threshold circuits 28, 29 and 30 are connected to electronic memory-units 31, 32 and 33 respectively which are themselves connected respectively to digital indication systems 34, 35 and 36.

The cuff is connected to an electronic absolute pressure gauge 37 comprising a Wheatstone bridge composed of piezo-resistances, this gauge being itself connected to an electronic amplifier 38 which is the same type as those mentioned above.

The amplifier 38 is connected to a numerical voltmeter 39 attached to the three electronic memory-units 31, 32 and 33.

The indication system 34 shows systolic pressure, the indication system 35 mean pressure and the indication system 36 diastolic pressure.

The apparatus thus conceived for determining and indicating arterial pressure functions as follows.

The cuff 1 is placed around a limb of the subject. The tap 5 being, for example, open, the pump 7 is started and the cuff is inflated until a pressure is reached in the interior of the latter which is higher than the systolic pressure of the subject.

The cuff is then deflated, at a slow and constant speed, from the initial suprasystolic pressure to an infradiastolic pressure. The deflation speed will be such that the passage from suprasystolic pressure to infradiastolic pressure will last, for example, from 15 to 20 seconds.

The differential pressure gauge 3 measures, at each instant during the deflation operation, the difference between the pressures existing at poles 3a and 3b and, as described above, converts it to an electrical value. The electric impulses issuing from the amplifier 14 are then directed in their entirety to the dephasing unit 17 of the integrator 16 of "staircase-form" signals represented in FIG. 10. The dephasing unit 17 is composed of a condenser and an amplifier without counter-reaction into which the electric signal penetrates by the negative entry.

The dephased signal of the value $\pi/2$ is then differentiated, with respect to time, by means of the element 18. The diode 20 then selects the positive part of the differentiated signal, which, after passing through the amplifier 21, opens the electronic gate 22.

In addition, the impulses issuing from the amplifier 14 are also directed to the diode 19 which selects the positive part and transmits it to the electronic gate 22.

In this way, the maximum value of the signal issuing from the amplifier 14 can be registered on the condenser 23 which gives the "staircase" graduations of which the height is proportional to the amplitude of the signal issuing from this amplifier.

The amplifier 24 mounted as an adaptor of impedance enables the difference in potential at the poles of the condenser 23 to be read and to be retransmitted as low impedance to the differentiator 25.

At the outlet of the differentiator 25, the signal is transmitted both to the amplitude threshold systems 28 and 29 and to the second integrator 26 of "staircase-form" signals which is identical to the integrator 16. However, in this second integrator 26, the electric signal penetrates into the amplifier without counter-reaction through the positive entry and not through the negative entry.

A short impulse is emitted by the circuit 28 as soon as an impulse of greater amplitude than the programmed amplitude reaches it. The effect of this is to block the electronic memory-unit 31. Following this, the electronic memory-unit 32 and then the electronic memory-unit 33 are blocked in their turn in the same way i.e. as soon as a brief impulse reaches them from circuits 29 and 30 respectively.

Furthermore, while the cuff is being deflated, the instantaneous pressures present in the cuff are converted to a continuous electrical value by the electronic absolute pressure gauge 37. This electrical value is then amplified by passing through the element 38 and directed to a numerical voltmeter 39 where it is transformed into a digital indication. The digital information is then transmitted to the three memory-units 31, 32 and 33.

When they are blocked, as described above, the memory-units show on the digital indication systems 34, 35 and 36 respectively the systolic mean and diastolic pressures of the subject.

In order to monitor the variations in arterial pressure occurring between two measurements of the latter, it is possible to connect the amplifier 14 to an integrator of classical design followed by a system for detecting variations in amplitude as described in connection with FIG. 8. Similarly, it is possible to connect the integrator 16 of "staircase-form" signals to a system for detecting variations in amplitude.

We claim:

1. A process for the periodical and automatic determination and indication of the systolic and mean pressures of a subject comprising the steps of applying a counter-pressure by a pressure applying means to a part of the body of the subject, varying the counter-pressure from a pressure above the systolic pressure of the subject to a pressure below the diastolic pressure of the subject, converting the shock wave produced by intra-arterial phenomena to an electrical signal by means of an electronic differential pressure gauge having at least one pole thereof coupled to the counter-pressure-applying means so that the intra-arterial phenomena producing variations in the counter-pressure excercised by the counter-pressure applying means are picked up by the electronic differential pressure gauge and converted to an electrical signal having a value which is continuous and proportional to the intra-arterial phenomena, sensing the instantaneous absolute counter-pressure excercised by the counter-pressure-applying means in a continuous manner and converting the instantaneous absolute counter-pressure to a second electrical signal by means of an electronic absolute pressure gauge connected to said pressure-applying means, the second electrical signal being supplied in a continuous manner and having an amplitude which is proportional to the amplitude of the pressure received, obtaining and indicating at the two points characterizing the curve of variation of the value of the electrical signal issuing from the electronic differential pressure gauge as a function of the counter-pressure excercised by the counter-pressure-applying means the two values of the counter-pressure excercised by the counter-pressure applying means which correspond to said two points and which indicate the systolic and mean pressures, wherein the step of obtaining and indicating the data at the two points characterizing the curve of variation of the value of the electrical signal which correspond to the systolic pressure and mean pressure, respectively, includes the step of integrating to "staircase-form" signals of the electrical signal issuing from the electronic differential pressure gauge, the amplitude of the graduations of the "staircase-form" signals being proportional to the difference between the amplitudes of said electrical signal at two successive samples, differentiating said "staircase-form" signals with respect to time in order to give a series of positive electric impulses and a series of negative electric impulses, comparing said impulses with two previously programmed amplitude thresholds in order to identify the two impulses corresponding to said two points, and enabling an electronic member unit to read said second electrical signal representative of said absolute pressure when said impulses have a predetermined relationship to said threshold to thereby determine the systolic and mean pressures.

2. A process according to claim 1 further including the step of obtaining and indicating the diastolic pressure by integrating to second "staircase-form" signals the amplitudes of the series of negative electric impulses, the amplitude of the second "staircase-form" signals graduations being proportional to the differences between the amplitudes of two successive negative electric impulses and by differentiating the second "staircase-form" signals with respect to time, and sampling said second signal representative of the absolute pressure when said differentiated second "staircase-form" signal reaches a predetermined threshold.

3. A process according to claim 1 wherein the "staircase-form" signals are obtained by applying the electrical signals issuing from the electronic differential pressure gauge to an electronic circuit composed of a condenser and an amplifier, differentiating, with respect to time, the signal issuing from said electronic differential pressure gauge, and selecting the positive part of the differentiated signal in order to open an electronic gate to which is applied the electrical signal issuing from the said electronic differential pressure gauge, to enable "staircase-form" signals to be registered on the condenser.

4. Apparatus for externally measuring the circulatory parameters of a subject including the systolic, means and diastolic pressures, comprising means for applying pressure to a part of the body of the subject, an electronic differential pressure gauge having two poles, an airtight air-reservoir having an inlet and an outlet, a Y-shaped tube coupling said pressure-applying means to one pole of said electronic differential pressure gauge and the other branch coupling said pressure-applying means to said inlet of said air-reservoir, an air pump and a bleed valve coupled to the air-reservoir and the pressure-applying means the outlet of said air-reservoir being connected to the other pole of the differential pressure gauge, an electronic absolute pressure gauge coupled to the pressure applying means, three electronic memory units, means coupling said absolute pressure gauge to said memory units, means coupled to said memory units for displaying the contents thereof, means for integrating to "staircase-form" the signals provided by said differential pressure gauge, the amplitude of the "staircase-form" signals being proportional to the amplitudes of the signals issuing from said differential pressure gauge, said apparatus further comprising means for differentiating the "staircase-form" signals with respect to time, threshold means having three predetermined amplitude thresholds, said differentiating means being coupled to said threshold means, said threshold means being connected to said three electronic memory units and operative to cause one of said memory units to store a value proportional to the absolute pressure read by said absolute pressure gauge each time said differentiated "staircase-form" signal has a predetermined amplitude relationship to one of said three amplitude thresholds.

5. Apparatus according to claim 4 wherein two of said predetermined amplitude thresholds correspond to the systolic pressure and the mean pressure, respectively.

6. Apparatus according to claim 4 further including second means coupled to said differentiating means for integrating to "staircase-form" said differentiated "staircase-form" signals, and second differentiating means interposed between said second integrating means and said threshold means and causing said threshold means to render one of said memory units operative to read the absolute pressure corresponding to the diastolic pressure.

7. Apparatus according to claim 4 further including means coupled to said differential pressure gauge for integrating, with respect to time, the electrical signals provided by said differential pressure gauge and adjustable threshold alarm means responsive to the variations in amplitude of the integrated signals, said alarm means being operative to provide an alarm in response to predetermined variations in arterial pressure.

8. Apparatus according to claim 4 further including means coupled to said integrating means for detecting with adjustable thresholds the variations in amplitude of the integrated electrical signals and for setting off an alarm in response to predetermined variations in arterial pressure.

9. Apparatus according to claim 4 further including means coupled to said electronic differential pressure gauge for providing an indication of the shape, amplitude and frequency of the electrical signals provided by said electronic differential pressure gauge.

10. Apparatus according to claim 4 wherein said means for integrating to "staircase-form" signals includes an input and an output, a gate, a first diode coupling said gate to said input, a condenser coupled to said gate and means coupling said gate and said condenser to said output, said means for integrating to "staircase-form" signals further including a 180° phase shift network coupled to said input, a differentiator coupled to said 180° phase shift network and means including a second diode coupling said differentiator to said gate, said 180° phase shift network, said differentiator and said means coupling said differentiator to said gate being operative to render said gate operative to periodically pass signals from said first diode to said condenser.

11. A method for automatically determining the systolic and mean pressures of a subject comprising the steps of:
applying a counter-pressure to a part of the body of the subject;
gradually varying the applied counter-pressure from a value above the systolic pressure of the subject to a value below the diastolic pressure of the subject;
continuously sensing the counter-pressure variations in the applied pressure resulting from the intra-arterial pressure variations of the subject as a function of the applied counter-pressure;
continuously sensing the instantaneous absolute counter-pressure applied to the subject;
determining the instantaneous slope of the pressure variations as a function of counter-pressure as the counter-pressure is gradually reduced from above the systolic pressure to below the diastolic pressure of the subject;
measuring the value of the absolute instantaneous counter-pressure applied to the subject when the slope exceeds a first positive threshold, said measured instantaneous counter-pressure being indicative of the systolic pressure of the subject; and
measuring the absolute instantaneous counter-pressure applied to the subject when said slope changes from a positive value to a negative value, said measured instantaneous counter-pressure being indicative of the mean pressure of the subject.

12. A method as recited in claim 11 further including the step of determining the diastolic pressure of the subject, said step including the steps of determining the second derivative of the pressure variation as a function of counter-pressure as said counter-pressure is varied from above the systolic pressure to below the diastolic pressure of the subject and measuring the absolute instantaneous pressure when said second derivative exceeds a predetermined negative threshold, said measured instantaneous absolute pressure being indicative of the diastolic pressure of the subject.

13. Apparatus for automatically determining the systolic and mean pressures of a subject comprising:
means for applying a gradually varying counter-pressure to a subject, said counter-pressure applying means being operative to vary said counter-pressure from a value above the systolic pressure of the subject to a value below the diastolic pressure of the subject;
means for continuously sensing counter-pressure variations in the applied pressure resulting from the intra-arterial pressure variations of the subject as a function of applied counter-pressure;
means for continuously sensing the instantaneous absolute counter-pressure applied to the subject;
differentiating means responsive to said counter-pressure variation sensing means for providing an indication of the instantaneous slope of the pressure variations as a function of applied counter-pressure as the counter-pressure is gradually reduced from above the systolic pressure to below the diastolic pressure of the subject; and
means responsive to said differentiating means coupled to said absolute pressure sensing means for measuring the absolute pressure when said slope exceeds a first predetermined threshold, said measured instantaneous counter-pressure being indicative of the systolic pressure of the subject, said absolute pressure measuring means being further responsive to a change in the slope of said pressure variations for rendering said absolute pressure measuring means operative to measure said absolute pressure when said slope changes from a positive slope to a negative slope, said last measured absolute pressure being indicative of the mean pressure of the subject.

14. Apparatus as recited in claim 13 further including means for measuring the diastolic pressure of the subject, said diastolic pressure measuring means including means operatively coupled to said differentiating means for determining the second derivative of the pressure variations of the subject as a function of the applied counter-pressure as said counter-pressure is varied from above the systolic pressure to below the diastolic pressure, said second derivative determining means being further coupled to said instantaneous absolute counter-pressure sensing means for measuring said absolute instantaneous counter-pressure when said second derivative exceeds a predetermined negative threshold, said measured instantaneous absolute pressure when said second derivative exceeds said predetermined negative threshold being indicative of the diastolic pressure of the subject.

* * * * *

UNITED STATES PATENT AND TRADEMARK OFFICE
CERTIFICATE OF CORRECTION

PATENT NO. : 4,177,801
DATED : December 11, 1979
INVENTOR(S) : HENRI GRANDGIRARD and PIERRE F. SERRES It is certified that error appears in the above—identified patent and that said Letters Patent are hereby corrected as shown below:

On the first page of the patent, the name of the primary inventor should be changed from "Henri Grangirard" to --Henri Grandgirard--.

In FIG. 10 of the drawing, the designation of block 17 should be changed from "180°" to --90°--

Signed and Sealed this

First Day of April 1980

[SEAL]

Attest:

SIDNEY A. DIAMOND

*Attesting Officer*     *Commissioner of Patents and Trademarks*